United States Patent
Dubois et al.

(10) Patent No.: US 6,384,276 B2
(45) Date of Patent: May 7, 2002

(54) PROCESS FOR THE PREPARATION OF LACTIC ACID BY EVAPORATIVE CRYSTALLISATION

(75) Inventors: Eric Dubois, Lestrem; Catherine Fouache, Sailly/Labourse, both of (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 09/863,104

(22) Filed: May 22, 2001

(30) Foreign Application Priority Data

May 23, 2000 (FR) .............................. 00 06586

(51) Int. Cl.⁷ .............................. C07C 59/08
(52) U.S. Cl. ................ 562/589; 562/515; 435/139
(58) Field of Search ................ 562/515, 589; 435/139

(56) References Cited

U.S. PATENT DOCUMENTS

| | | | | |
|---|---|---|---|---|
| 1,594,843 A | * | 8/1926 | Lawrie | |
| 2,024,565 A | * | 12/1935 | Braun | 260/119 |
| 5,210,296 A | | 5/1993 | Cockrem et al. | 562/589 |
| 5,641,406 A | | 6/1997 | Sarhaddar et al. | 210/656 |
| 5,681,728 A | * | 10/1997 | Miao | 435/136 |

FOREIGN PATENT DOCUMENTS

| | | |
|---|---|---|
| DE | 222741 | 6/1910 |
| EP | 0 393 818 | 2/1990 |
| EP | 0 849 252 | 12/1997 |
| GB | 907321 | 7/1958 |

OTHER PUBLICATIONS

"Resolution of Lactic Acid into its Optically Active Compounds" Purdie, Walker; J. Chem. Soc. vol. 61 pp 754–765 (1892).*

"The Preparation of Crystalline Lactic Acid" Borsook, Huffman; J. Biol. Chem. vol. 102 pp 449–459 (1933).*

Hongo M et al. "Novel Method of Lactic Acid Production by Electrodialysis Fermentation", Applied and Environmental Microbiology, USA, vol. 52, No. 2, pp. 314–319 (Aug. 1986).

* cited by examiner

Primary Examiner—Gary Geist
Assistant Examiner—Zachary Tucker
(74) Attorney, Agent, or Firm—Henderson & Sturm LLP

(57) ABSTRACT

The invention relates to a process for the preparation of high purity lactic acid from an aqueous solution containing said acid in the form of salt(s), characterised in that the aqueous solution is treated with a strong acid in order to liberate lactic acid in the free form and to produce salts of the corresponding strong acid, said salts of the strong acid are crystallised by evaporative crystallisation and lactic acid is recovered in the free form in solution.

11 Claims, No Drawings

PROCESS FOR THE PREPARATION OF LACTIC ACID BY EVAPORATIVE CRYSTALLISATION

The present invention relates to a particular process for the preparation of lactic acid from an aqueous solution containing lactic acid, in the form of salt(s) particularly from a fermentation medium.

The present invention also relates to a process for the preparation of lactic acid, the purity of which is such that it may be used not only in sectors such as food applications, the chemical and agrochemical industries, plastics, cosmetics, but above all in pharmaceutical applications.

According to the invention, a "high purity lactic acid" means a grade of lactic acid which satisfies the pharmaceutical standards of purity (thermal stability test of "The United States Pharmacopeia") and complies with the standards of the "Food Chemicals Codex".

The preparation of an aqueous solution of lactic acid in the form of salt(s) usually means the fermentation of microorganisms of the Lactobacillus type (such as *L. acidophilus, L. delbrüeckii* or *L. pentosus*), Lactococcus, Enterococcus, Pediococcus, Vagococcus, Tetragenococcus, Aerococcus, Rhizopus, Bacillus (such as *B. coagulans*), Streptococcus, Bifidobacterium . . .

Indeed, it is known that the growth of most of these lactic acid-producing microorganisms, and even the viability thereof, is inhibited by the fall in the pH of the fermentation medium, this strong acidification of the medium being brought about by the production of organic acids, including lactic acid itself.

It is necessary, therefore, to control the pH and it is generally accepted that this must be kept at a value in the range from 4 to 7, preferably higher than 4.5, for example, in the range from 5.5 to 6.5, by adding bases such as alkali metal or alkaline earth metal hydroxides, carbonates or bicarbonates.

Lactic acid is therefore present in these fermentation media in the form of salts (lactates of sodium, potassium, calcium or ammonium, alone or in mixture, depending on the base selected for controlling the pH of the fermentation medium).

Consequently, all the methods for recovering lactic is acid from aqueous solutions containing them, and particularly if this aqueous solution is composed of a fermentation medium, have to overcome the same difficulties, i.e. carrying out the separation of the salt(s) of lactic acid, the microorganisms which produced them and the impurities of the fermentation medium (unconsumed sugars and proteins, and inorganic salts of various kinds) and, moreover, carrying out the conversion of the salts of lactic acid to lactic acid in the free form, which also then requires the removal of the corresponding base produced.

Various methods have been proposed for recovering lactic acid from an aqueous solution, and particularly from a fermentation medium.

All these methods are based on the same principle, i.e. extraction of the lactic acid as such from the fermentation medium.

However, as has been shown before, lactic acid is present in the form of a salt (lactate).

If the control of the pH of the fermentation medium is achieved by carbonates or bicarbonates of calcium, lactic acid in the free form may be recovered, for example, by acidification of the medium with sulphuric acid.

In this case, the reaction gives rise to the formation of calcium sulphates (gypsum) which precipitate and to the release of lactic acid in the free form which may then be adsorbed, for example, on a suitable support and then desorbed.

As described in EP 849.252, in order to obtain high purity lactic acid, multiple crystallisations are generally carried out, firstly of the calcium lactates in order to remove the soluble impurities from the fermentation medium, and then of the calcium sulphates liberated after treatment with sulphuric acid.

These crystallisation steps are followed by numerous complementary extraction steps with ether or by a long chain amine, combined with purification steps by ion exchange chromatography, electrodialysis, and hydrolysis reactions in order to obtain a high purity lactic acid.

The first disadvantage of this method which is, admittedly, effective in terms of yield, is the high sulphuric acid consumption and above all the production of large amounts of gypsum which poses serious problems in terms of waste treatment and biodegradability for the environment.

The second disadvantage is the complexity and the high number of steps required to obtain a high purity lactic acid.

Other methods have, therefore, been proposed, leading to the crystallisation of salts of lactic acid.

For example, U.S. Pat. No. 5,641,406 describes, after the step involving the precipitation of calcium lactates with sulphuric acid and the treatment with ferrocyanide or hexaferrocyanide salts to remove the copper and iron ions, the decolourisation of the "crude" lactic acid thus obtained with activated charcoal, and after the subsequent purification steps to remove all the residual salts, the concentration by evaporation and hence crystallisation of the lactates.

Here again, this process suffers from a large number of purification steps and the handling of toxic chemicals.

A solution to these problems was given in U.S. Pat. No. 5,210,296 by the use of a process consisting of
continuous acidification of an aqueous solution containing ammonium lactate in the presence of an alcohol having 4 to 5 carbon atoms used as a diluent, with sulphuric acid (or any other strong acid),
removal of water from the acidified mixture by distillation of the water/alcohol azeotrope and in a simultaneous or sequential manner, removal of the ammonium sulphate crystals produced (or salts of strong acid produced),
distillation and hydrolysis of the lactic acid ester liberated in order to produce a free lactic acid having a purity of more than 99.5%.

However, the difficulty of this process lies in particular in the need to remove the ammonium sulphates. It is mentioned that it is imperative to use alcohols having 4 to 5 carbon atoms (namely n-butanol in this case) in order to obtain sufficiently coarse ammonium sulphate crystals to facilitate their separation by simple filtration of the reaction medium.

As a result, it is then possible to produce an azeotropic water/n-butanol mixture which will be easy to remove by continuous distillation.

It is still necessary, therefore, to proceed via the lactic acid ester, the distillation and hydrolysis thereof in order to obtain a lactic acid of satisfactory purity.

Consequently, the processes of the prior art all still suffer in practice from this succession of numerous and cumbersome steps which make the purification of lactic acid from an aqueous solution containing lactic acid in the form of salt(s) particularly long and tedious.

It is evident from the above that there is an unsatisfied need for a simpler and cheaper process which permits the separation, concentration and purification of a high purity lactic acid with an excellent yield from an aqueous solution containing lactic acid in the form of salt(s).

Anxious to develop a process which will satisfy the practical limitations better than those that already exist, the Applicant company observed that this objective could be achieved by a process which consists in carrying out, on an aqueous solution containing lactic acid in the form of salt(s), an acidification of said aqueous solution and crystallisation under particular conditions of the salts of the strong acid thus produced, which makes it possible to directly obtain a high quality, free lactic acid.

The Applicant company has thus overcome the technical prejudices whereby the use of a crystallisation step in a protocol for the purification of lactic acid from an aqueous solution containing lactic acid in the form of salt(s):

must mean crystallisation of the salt of lactic acid in order to extract it from said medium, and only then the acidification thereof to precipitate the salts of the strong acid and to produce lactic acid in the free form, or, if it entails crystallisation of the salts of the strong acid, this must necessarily be in an alcoholic medium in order to produce crystals of a sufficient size to allow their removal from said medium with the simultaneous formation of the lactic acid ester.

The process for the preparation of high purity lactic acid from an aqueous solution containing lactic acid in the form of salt(s) according to the invention of the Applicant company is characterised in that:

the aqueous solution is treated with a strong acid in order to liberate lactic acid in the free form and to produce corresponding salts of the strong acid, said salts of the strong acid are crystallised by evaporative crystallisation, the lactic acid is recovered in the free form in solution.

The first step of the process according to the invention consists in treating the aqueous solution containing lactic acid in the form of salt(s) using a strong acid in order to liberate lactic acid in the free form and to produce corresponding salts of the strong acid.

In a preferred embodiment of the process according to the invention, an aqueous solution containing lactic acid in the form of salts is used, said solution being obtained from a fermentation medium for a lactic acid-producing microorganism. Said microorganisms are removed from this fermentation medium by any method known to the skilled person.

The lactic acid-producing microorganisms are selected without discrimination and particularly from the group consisting of Lactobacillus, Lactococcus, Enterococcus, Pediococcus, Vagococcus, Tetragenococcus, Aerococcus, Rhizopus, Bacillus, Streptococcus and Bifidobacterium. The composition of their fermentation medium is widely described in the prior art.

The pH of the fermentation medium is adjusted to a value in the range from, for example, 5 to 7, by continuously feeding the fermentation medium with a base selected preferably from the group consisting of NaOH, $MgCO_3$, $Na_2CO_3$, $Ca(OH)_2$, $CaCO_3$, KOH and $NH_4OH$, and is preferably $NH_4OH$ or NaOH.

Lactic acid is present in the form of an alkaline earth metal salt selected from the group consisting of ammonium, magnesium, calcium, sodium and potassium and is preferably ammonium or sodium.

According to the invention, the lactic acid contained in the fermentation medium is, therefore, partly or wholly in the form of ammonium salt(s) or sodium salt(s).

The separation of said lactic acid-producing microorganisms from the other constituents of the fermentation medium may consist in microfiltration, centrifugation or precipitation of said microorganisms by flocculating agents. These methods may also be combined.

In the process according to the invention, a microfiltration method is preferred, said method using a microfiltration membrane the porosity of which is adapted to the size of the microorganisms considered, for example, TECHSEP membranes having a porosity of 0.1 μm for lactic acid-producing microorganisms of the Lactobacillus type.

There follows advantageously a step to remove nonionic or slightly ionic constituents from the fermentation medium that are still present in the aqueous solution from which the microorganisms have been removed, by a method selected from the group of nanofiltration and/or conventional electrodialysis methods, as will be illustrated by examples below.

These nonionic constituents mean, in this case, chiefly proteins and sugars which have not been fully assimilated by the lactic acid-producing microorganisms.

The conventional electrodialysis step consists, for example, in treating a fermentation medium from which its biomass has been removed, containing from 5 wt. % to 15 wt. % of lactate and coproducts of fermentation, in a conventional electrodialysis module in order to recover a solution enriched with lactates and salts and from which nonionic or slightly ionic compounds have been removed.

The solution of ammonium or sodium lactate which is then recovered at the outlet of conventional electrodialysis has, for example, a dry matter content in the range from 4 wt. % to 15 wt. %, preferably from 5 wt. % to 10 wt. %.

This solution is then advantageously concentrated to obtain a dry matter content of at least 30 wt. %, preferably from 30 wt. % to 50 wt. %, by any method known to the skilled person.

The solution of ammonium or sodium lactate thus concentrated is then acidified using a strong acid. The acid selected is advantageously 98% sulphuric acid, and the pH of the reaction medium is brought to a value in the range from 2 to 4, preferably to a value of 2.5.

This acidification reaction leads to the separation of lactic acid in the free form and to the production of corresponding salts of the strong acid, namely ammonium sulphates or sodium sulphates in this case.

The second step of the process according to the invention then consists in crystallising, by evaporation, said salts of the strong acid and more particularly the ammonium or sodium sulphates in this case.

This step consists in carrying out evaporative crystallisation of the aqueous solution containing the mixture of free lactic acid and ammonium sulphates or sodium sulphates, in order to allow the specific crystallisation of the ammonium or sodium sulphates, leaving the free lactic acid in solution in the aqueous mother liquor.

The reaction is stopped when the system no longer appears to evaporate water.

The crystalline mass thus obtained may then be separated from the free lactic acid in solution by a method selected from the group of filtration and centrifugation methods, and is preferably the method of centrifugation.

The evaporative crystallisation conditions are selected in such a way as to obtain a fraction composed of free lactic acid having a dry matter content having a value at least equal to 70 wt. %, preferably at least equal to 90 wt. %, and a fraction containing at least 90 wt. % of ammonium or sodium sulphate in the crystalline form, as will be shown by examples below.

Finally, a final step may be carried out, consisting of removing the last impurities present in the fraction composed of free lactic acid having a dry matter content reduced to a value at least equal to 10 wt. %, preferably at least equal to 25 wt. %. Said impurities are composed chiefly of ions, for example, ammonium, which the various above-mentioned treatments were unable to remove completely, and of residual sulphates.

The choice is thus made advantageously to:
a) demineralise the solution thus obtained over a strong cationic resin followed by a slightly basic anionic resin,
b) concentrate the lactic acid thus purified.

The first step consists in removing all the inorganic salts by passing them over two resins: a strong cationic resin then a weak anionic resin.

In the second step, the resulting solution is concentrated in order to bring it to a dry matter content at least equal to 90 wt. %.

Surprisingly and unexpectedly, the analysis of the lactic acid separated and purified in this way revealed a quality which satisfies the pharmaceutical standards of purity (conforming to "The United States Pharmacopeia") and complies with the standards of the "Food Chemicals Codex".

Other features and advantages of the invention will become apparent from reading the examples below. They are, however, given here only by way of non-limiting example.

EXAMPLE 1

The starting medium was a Lactococcus fermentation medium containing 82 g/l of lactic acid in the form of ammonium lactates, 0.8 % of proteins and 0.5 % of residual sugars, from which medium its microorganisms had been removed by microfiltration. 650 l of this solution fed an electrodialysis module of the EUR6B EURODIA type fitted with ion exchange membranes (NEOSEPTA-TOKUYAMA SODA) of the CMX-S cationic type and AMX Sb anionic type having an active surface area of 5.6 m², following the operating parameters defined by the manufacturer, at 35° C., in such a way as to obtain a rate of recovery of lactic acid in the form of ammonium lactates of 98%.

The solution electrodialysed in this way made it possible to recover, in the fraction enriched with ammonium lactates, 90% of lactic acid in its salt form.

This solution was concentrated by evaporation under vacuum at a pressure of 0.9 bar and at a temperature of 60° C. in a falling film evaporator of the WIEGAND type.

The concentrated solution thus obtained (120 l with a content of 40 wt. % based on dry product) was acidified with 98% $H_2SO_4$ to a pH of 2.5.

This acidified solution then underwent an evaporative crystallisation step consisting of drawing off, under vacuum, the residual water with agitation at a fixed pressure of 0.8 bar at a temperature of 60° C.

Evaporative crystallisation was carried out for 10 h.

At the end of evaporative crystallisation, 52 kg of a crystalline mass containing 36 wt. % of individual ammonium sulphate crystals were obtained.

A centrifugation step in a ROUSSELET type horizontal centrifuge allowed the separation of the ammonium sulphate crystals from the lactic solution in the purified free form.

Said solution of lactic acid was recovered in a dry matter content of 95% for a lactic acid concentration of 95%.

Said solution was then reduced to a dry matter content of 25 wt. % and demineralised over strong cationic and weak anionic resins by any method known to the skilled person.

The lactic acid demineralised in this way was concentrated by evaporation in order to bring it to a dry matter content of 90 wt. %.

The lactic acid separated and purified in this way revealed a quality which satisfies the pharmaceutical standards of purity (in conformity with "The United States Pharmacopeia") and complies with the standards of the "Food Chemicals Codex". More particularly, the analysis revealed an L lactic acid content of 97.5%, an ash content of less than 0.1% Moreover, the tests for "readily carbonisable substance", "organic acids" and "reducing sugar content" comply with the required specifications.

EXAMPLE 2

The procedure was the same as that described in example 1, starting with a Lactococcus fermentation medium containing 80 g/l of lactic acid in the form of sodium lactates, 0.9% of proteins and 0.4% of residual sugars, from which medium its microorganisms had been removed by microfiltration.

207 l of this solution fed an electrodialysis module of the EUR6 B EURODIA type fitted with ion exchange membranes (NEOSEPTA-TOKUYAMA SODA) of the CMX-S cationic type and AMX Sb anionic type having an active surface area of 5.6 m², following the operating parameters defined by the manufacturer, at 35° C., in such a way as to obtain a rate of recovery of lactic acid in the form of sodium lactates of 97%

The solution electrodialysed in this way made it possible to recover, in the fraction enriched with sodium lactates, 90% of lactic acid in its salt form.

This solution was concentrated by evaporation under vacuum at a pressure of 0.9 bar and at a temperature of 60° C. in a falling film evaporator of the WIEGAND type.

The concentrated solution thus obtained (41.5 l with a content of 40 wt. % based on dry product) was acidified with 98% $H_2SO_4$ to a pH of 2.5.

This acidified solution then underwent an evaporative crystallisation step consisting of drawing off, under vacuum, the residual water with agitation at a fixed pressure of 0.8 bar at a temperature of 60° C.

Evaporative crystallisation was carried out for 10 h.

At the end of evaporative crystallisation, 19 kg of a crystalline mass containing 40 wt. % of individual sodium sulphate crystals were obtained.

A centrifugation step in a ROUSSELET type horizontal centrifuge allowed the separation of the sodium sulphate crystals from the lactic solution in the purified free form.

Said solution of lactic acid was recovered in a dry matter content of 95% for a lactic acid concentration of 95%.

Said solution was then reduced to a dry matter content of 25 wt. % and demineralised over strong cationic and weak anionic resins by any method inherently known to the skilled person.

The lactic acid demineralised in this way was concentrated by evaporation in order to bring it to a dry matter content of 90 wt. %.

The lactic acid separated and purified in this way revealed a quality which satisfies the pharmaceutical standards of purity (in conformity with "The United States Pharmacopeia") and complies with the standards of the "Food Chemicals Codex". More particularly, the analysis revealed an L lactic acid content of 98%, an ash content of less than 0.1%. Moreover, the tests for "readily carbonisable substance", "organic acids" and "reducing sugar content" comply with the required specifications.

What is claimed is:

1. A process for the preparation of high purity lactic acid from an aqueous solution containing said acid in the form of salt(s), wherein:

the aqueous solution is treated with a strong acid in order to liberate lactic acid in the free form and to produce corresponding salts of the strong acid, said salts of the strong acid are crystallised by evaporative crystallisation, lactic acid is recovered in the free form in solution.

2. A process according to claim 1, wherein the aqueous solution containing lactic acid in the form of salt(s) is a fermentation medium from which its microorganisms have been removed.

3. A process according to claim 2, wherein the fermentation medium undergoes an electrodialysis step in order to obtain an electrodialysed aqueous solution from which the nonionic constituents of the fermentation medium have been removed.

4. A process according to claim 3, wherein the electrodialysed aqueous solution is concentrated to a dry matter content of at least 30%.

5. A process according to claim 3, wherein the electrodialysed aqueous solution is concentrated to a dry matter content in the range from 30% to 50%.

6. A process according to claim 1, wherein in the strong acid is 98% sulphuric acid.

7. A process according to claim 1, wherein the crystals of salts of the strong acid are separated from lactic acid in the free form by a method selected from the group of filtration and centrifugation methods.

8. A process according to claim 1, wherein the crystals of salts of the strong acid are separated from lactic acid in the free form by the centrifugation method.

9. A process according to claim 1, wherein lactic acid is present in the form of a salt from the group consisting of ammonium salt, magnesium salt, calcium salt, sodium salt and potassium salt.

10. A process according to claim 1, wherein the salt is ammonium lactate.

11. A process according to claim 1, wherein the salt is sodium lactate.

* * * * *